United States Patent
Cotner et al.

[11] Patent Number: 6,019,101
[45] Date of Patent: *Feb. 1, 2000

[54] NASAL AIR MASK

[75] Inventors: Ronald L. Cotner, Derry; Thomas E. Asacker, Exeter, both of N.H.

[73] Assignee: SleepNet Corporation, Manchester, N.H.

[*] Notice: This patent issued on a continued prosecution application filed under 37 CFR 1.53(d), and is subject to the twenty year patent term provisions of 35 U.S.C. 154(a)(2).

[21] Appl. No.: 08/741,524

[22] Filed: Oct. 31, 1996

[51] Int. Cl.$^7$ .................................................. A62B 18/08
[52] U.S. Cl. ............................ 128/207.13; 128/206.18; 128/206.24; 128/206.27
[58] Field of Search ................ 128/207.13, 201.11, 128/203.29, 204.26, 205.25, 206.18, 206.24, 206.25, 206.26, 206.27, 207.11, 207.18, 201.18, 201.23, 207.17; 2/9, 206

[56] References Cited

U.S. PATENT DOCUMENTS

| | | | |
|---|---|---|---|
| Re. 35,339 | 10/1996 | Rapoport | 128/205.25 |
| D. 156,060 | 11/1949 | Wade . | |
| D. 161,337 | 12/1950 | Hill | D24/110.1 |
| D. 248,497 | 7/1978 | Slosek | D29/8 |
| D. 285,496 | 9/1986 | Berman | D29/8 |
| D. 310,431 | 9/1990 | Bellm | D29/8 |
| D. 335,322 | 5/1993 | Jones | D24/110.2 |
| 428,592 | 5/1890 | Chapmam | 128/205.25 |
| 1,206,045 | 11/1916 | Smith . | |
| 1,610,793 | 12/1926 | Kaufman | 128/206.18 |
| 1,632,449 | 6/1927 | McKesson | 128/207.13 |
| 2,248,477 | 7/1941 | Lombard . | |
| 2,254,854 | 9/1941 | O'Connell | 128/207.13 |
| 2,376,871 | 5/1945 | Fink . | |
| 2,540,567 | 2/1951 | Bennett | 128/206.26 |
| 2,625,155 | 1/1953 | Engelder | 128/146 |

(List continued on next page.)

FOREIGN PATENT DOCUMENTS

| | | | |
|---|---|---|---|
| 618807 | 4/1961 | Canada | 128/206.24 |
| 0623129 | 7/1961 | Canada | 128/206.24 |
| 0 549 299 A2 | 6/1993 | European Pat. Off. . | |
| 0 747 078 A2 | 12/1996 | European Pat. Off. . | |
| 0780018 | 4/1935 | France | 128/201.11 |

OTHER PUBLICATIONS

Healthdyne® Technologies Soft Series™ Mask advertisement, 1 page, undated.
Puritan Bennett Companion® Nasal CPAP Masks advertisement, 1 page, undated.
Respironics Inc. Monarch Mini Mask information sheet, 1 page, dated Feb. 26, 1996.
Lifecare® Form #544, 1 page, dated Jul. 1991.
Medical Industries America Universal Deluxe C.P.A.P. Headgear advertisement, 1 page, undated.
ResCare Sullivan® Bubble Mask™ System Series 3 advertisement, 3 pages, undated.

*Primary Examiner*—John G. Weiss
*Assistant Examiner*—V. Srivastava
*Attorney, Agent, or Firm*—Testa, Hurwitz & Thibeault, LLP

[57] ABSTRACT

Disclosed is a novel improved nasal mask useful for patients suffering from respiratory ailments such as sleep apnea syndrome. The mask includes a shell having a contoured portion circumscribing the nasal area and side wings through which a retention strap passes. A seal is disposed between the shell and the patient's face providing a large contact area to distribute retention forces and reduce facial pressure. Transmission of external loads to and torques induced in the shell are minimized by orienting inlets proximate side wings and supporting a supply conduit along the strap.

41 Claims, 4 Drawing Sheets

U.S. PATENT DOCUMENTS

| | | | |
|---|---|---|---|
| 2,693,178 | 11/1954 | Gilroy | 128/204.26 |
| 2,837,090 | 6/1958 | Bloom et al. | 128/146 |
| 2,868,196 | 1/1959 | Stampe. | |
| 2,902,033 | 9/1959 | Galleher, Jr. | 128/206.24 |
| 2,917,045 | 12/1959 | Schildkecht et al. | 128/141 |
| 2,931,356 | 4/1960 | Schwarz | 128/206.24 |
| 3,042,035 | 7/1962 | Coanda | 128/206.24 |
| 3,117,574 | 1/1964 | Replogle | D24/110.4 |
| 3,288,138 | 11/1966 | Sachs | D24/110.1 |
| 3,315,672 | 4/1967 | Cunningham et al. | 128/206.19 |
| 3,330,273 | 7/1967 | Bennett | 128/206.26 |
| 4,062,357 | 12/1977 | Laerdal | 128/146 |
| 4,167,185 | 9/1979 | Lewis | 128/206.24 |
| 4,201,205 | 5/1980 | Bartholomew | 128/205.25 |
| 4,231,363 | 11/1980 | Grimes | 128/205.25 |
| 4,266,540 | 5/1981 | Panzik et al. | 128/207.13 |
| 4,337,767 | 7/1982 | Yahata | 128/206.28 |
| 4,354,488 | 10/1982 | Bartos | 128/205.25 |
| 4,412,537 | 11/1983 | Tiger | 128/207.13 |
| 4,414,973 | 11/1983 | Matheson et al. | 128/206.15 |
| 4,417,575 | 11/1983 | Hilton et al. | 128/206.19 |
| 4,454,880 | 6/1984 | Muto et al. | 128/207.13 |
| 4,572,323 | 2/1986 | Randall | 181/129 |
| 4,593,688 | 6/1986 | Payton | 128/200.28 |
| 4,674,134 | 6/1987 | Lundin | 2/209 |
| 4,770,169 | 9/1988 | Schmoegner et al. | 128/207.13 |
| 4,799,477 | 1/1989 | Lewis | 128/206.24 |
| 4,807,617 | 2/1989 | Nesti | 128/205.12 |
| 4,856,118 | 8/1989 | Sapiejewski | 2/209 |
| 4,915,106 | 4/1990 | Aulgur et al. | 128/207.11 |
| 4,944,310 | 7/1990 | Sullivan | 128/848 |
| 4,960,121 | 10/1990 | Nelson et al. | 128/206.24 |
| 4,971,051 | 11/1990 | Toffolon | 128/206.26 |
| 4,989,271 | 2/1991 | Sapiejewski et al. | 2/209 |
| 5,003,631 | 4/1991 | Richardson | 2/6 |
| 5,003,633 | 4/1991 | Itoh | 2/9 |
| 5,018,519 | 5/1991 | Brown | 128/203.29 |
| 5,074,297 | 12/1991 | Venegas | 128/204.18 |
| 5,109,839 | 5/1992 | Blasdell et al. | 128/203.12 |
| 5,138,722 | 8/1992 | Urella et al. | 2/209 |
| 5,146,914 | 9/1992 | Sturrock | 128/203.11 |
| 5,181,506 | 1/1993 | Tardiff, Jr. et al. | 128/201.22 |
| 5,243,971 | 9/1993 | Sullivan et al. | 128/205.25 |
| 5,343,878 | 9/1994 | Scarberry et al. | 128/898 |
| 5,349,949 | 9/1994 | Schegerin | 128/206.24 |
| 5,400,781 | 3/1995 | Davenport | 128/205.25 |
| 5,429,683 | 7/1995 | Le Mitouard | 128/206.24 |
| 5,540,223 | 7/1996 | Starr et al. | 128/205.25 |
| 5,560,354 | 10/1996 | Berthon-Jones et al. | 128/205.25 |
| 5,570,684 | 11/1996 | Behr | 128/205.25 |
| 5,592,938 | 1/1997 | Scarberry et al. | 128/206.24 |
| 5,617,849 | 4/1997 | Springett et al. | 128/206.24 |
| 5,647,357 | 7/1997 | Barnett et al. | 128/206.24 |
| 5,657,752 | 8/1997 | Landis et al. | 128/207.13 |
| 5,660,174 | 8/1997 | Jacobelli | 128/206.24 |

NASAL AIR MASK

TECHNICAL FIELD

The present invention relates to respiratory apparatus and more specifically to a nasal mask useful for providing pressurized air or therapeutic gas to a patient suffering from an airflow limitation or other respiratory ailment.

BACKGROUND

Patients suffering from a variety of medical conditions require supplementary respiratory support. Depending on the nature and severity of the condition, this respiratory support can range from the provision of an elevated oxygen concentration cloud to the vicinity of the nose and mouth, to forced ventilation of the lungs by intubation of the trachea. In general, a supply of pressurized air or therapeutic gas is provided by a tube or conduit to a delivery apparatus designed to conform to particular body structure.

One style of delivery apparatus is a mask which provides the gas to the nasal area of the patient. Nasal masks are often employed in the treatment of sleep apnea syndrome, characterized by intermittent upper airway obstruction during sleep. Due to the resulting blood oxygen desaturation and frequent arousals from sleep, persons suffering from this condition are often unable to achieve deep sleep for extended periods and are chronically tired and physically compromised. In severe cases, cardio-pulmonary complications can arise or death during sleep may result.

Since nasal masks are often worn by persons in unmonitored environments for extended periods, such as in the home during sleep, the nasal mask should be comfortable to wear and conform well to the nasal area thereby defining a sealed chamber. If the mask is deemed too bulky, too heavy, or to fit poorly, the patient will either not wear the mask, wear the mask improperly, or only wear the mask occasionally when the discomfort associated with the respiratory condition exceeds the discomfort of wearing the mask.

One problem associated with nasal masks relates to the conformance of the mask to the nasal area, which is complexly contoured and differs from patient to patient. Customized masks manufactured to suit particular patients tend to be costly; therefore, masks for general use are made in several generic sizes, each size designed to accommodate a range of patients. If the mask does not form a good seal around the patient's nose, leakage can occur, reducing the effectiveness of the treatment. When poorly fitting masks are used with variably regulated air supply systems responsive to patient breathing, such as those developed for treating sleep apnea, mask leakage can induce improper system response which may exacerbate the patient's condition. Regulated air supply systems for treatment of sleep apnea are disclosed in Patent Cooperation Treaty international application number PCT/US93/05095 published on Dec. 9, 1993 as international publication number WO 93/24169; U.S. patent application Ser. No. 08/184,976 filed Jan. 24, 1994; U.S. patent application Ser. No. 08/331,030 filed Oct. 27, 1994 now U.S. Pat. No. 5,645,054; U.S. Pat. No. 5,199,424; U.S. Pat. No. 5,245,995; and U.S. Pat. No. 5,522,382, the disclosures of all of which are herein incorporated by reference.

One method of reducing leakage is to provide a compliant sealing flange or surface around a perimeter of the mask in combination with a strap to bias the mask into sealing engagement with the nasal contour of the patient. Typically, the greater the retention force applied by the strap, the better the seal; however, both the strap and the mask can cause excessive pressure on delicate areas resulting in irritation and patient discomfort.

The retention force required to prevent leakage is also a function of forces and torques induced in the mask. For example, the weight of the conduit supplying air or gas to the mask tends to pull the mask downward, away from the patient's nasal area, when the patient is sitting. Additionally, any movement of the head from side-to-side or up and down can cause lifting of an edge or sliding of the mask and strap. The more rapid the movement, the more pronounced the effect. Mask slippage and displacement are exacerbated in masks employing large diameter, heavy, or stiff tubes which deliver relatively large volumetric flow rates of air, such as those employed in sleep apnea treatment systems. Masks have been developed which employ a swivel attachment between the conduit and the shell. While these attachments can alleviate some movement induced forces, they are effective only within the planar degree of freedom of the swivel. These attachments are ineffective in reducing forces in other planes and do not address offsetting the weight of the conduit.

For nasal masks used by patients when sleeping, the strap and seal arrangement should also accommodate unconscious or reflexive head and body movements. The discomfort associated with masks which apply too much pressure to the head, neck, or nasal area discourage use of the mask during sleep when it is most needed. As a result, treatment is compromised and the patient is ill served by the apparatus.

Accordingly, there exists a need to overcome the limitations of known designs by providing an improved nasal mask which provides a consistent, reliable nasal area seal while being comfortable to wear. Other desirable features would include ease of manufacture and low cost.

SUMMARY OF THE INVENTION

An improved nasal mask is disclosed useful in a wide variety of applications including, but not limited to, respiratory apparatus employed for treatment of sleep apnea syndrome. In an exemplary embodiment, the nasal mask includes a compliant shell having a contoured portion configured to create a chamber around the nose of the patient. Two symmetrically disposed side wings extend from the contoured portion along the patient's cheeks and include slots at distal ends thereof through which a retention strap passes. A soft silicone filled bladder seals any leakage gap between the contoured portion of the shell and the patient's nasal area. The seal extends along the wings against the patient's cheeks providing a relatively large contact area with the patient's face. This configuration distributes the retention force applied by the strap through the side wings to both the nasal area and the cheeks, thereby reducing local pressure. The large contact area also improves conformance of the mask to the face, substantially eliminating leakage and reducing slippage for a given induced force.

The strap may be manufactured from an elastically compliant material in one or more pieces and forms a continuous loop when worn. The strap passes around the patient's neck, slidingly through the wing slots, and around the patient's head. The head cradling portion of the strap may be bifurcated along a length thereof, with one leg disposed about the rear of the head and the other about the top of the head. A length adjustment feature may be provided so that a single adjustment of the strap simultaneously adjusts both head and neck portions.

The strap may further includes one or more retainers for supporting an air supply conduit. The conduit may be connected to an air supply source at the top or rear of the patient's head and is routed along the strap to a side wing, terminating at an inlet connector located on the contoured portion of the shell. The retainers are sized to permit sliding of the conduit along its axis. The inlet is disposed advantageously proximate the centerline of the side wing and oriented such that a centerline thereof is substantially parallel to the wing centerline.

Accordingly, the weight of the conduit is supported directly by the strap, eliminating weight induced loads which would tend to displace the shell or require greater retention force. Further, the conduit moves with head movement, substantially eliminating movement induced forces and torques in the shell caused by the conduit. Any torques induced in the shell by conduit forces are minimized by keeping moment arms between the inlet, strap, and facial contact area very short. As a result, displacement of the shell is minimized and seal leakage substantially eliminated, while retention force is maintained at a comfortable level. Additionally, since the conduit is free to slide in the retainers and the strap is free to slide in the wing slots, extreme movements of the head can be accommodated and the mask can be comfortably worn during sleep without leakage which could adversely affect a responsive regulated air supply system.

The shell may include a plastically deformable nose clip, to conform the shell to the contour of the bridge of the nose, and additional inlets for mating with other air or therapeutic gas supply sources or for use in connecting the nasal chamber to diagnostic equipment for patient monitoring. The shell also typically includes one or more outlets for venting the chamber to ambient to provide controlled venting of the chamber and to permit substantially unrestricted exhalation. These outlets may be simple apertures.

BRIEF DESCRIPTION OF THE DRAWINGS

The invention, in accordance with preferred and exemplary embodiments, together with further advantages thereof, is more particularly described in the following detailed description taken in conjunction with the accompanying drawings in which.

DETAILED DESCRIPTION OF THE INVENTION

Figure 1:
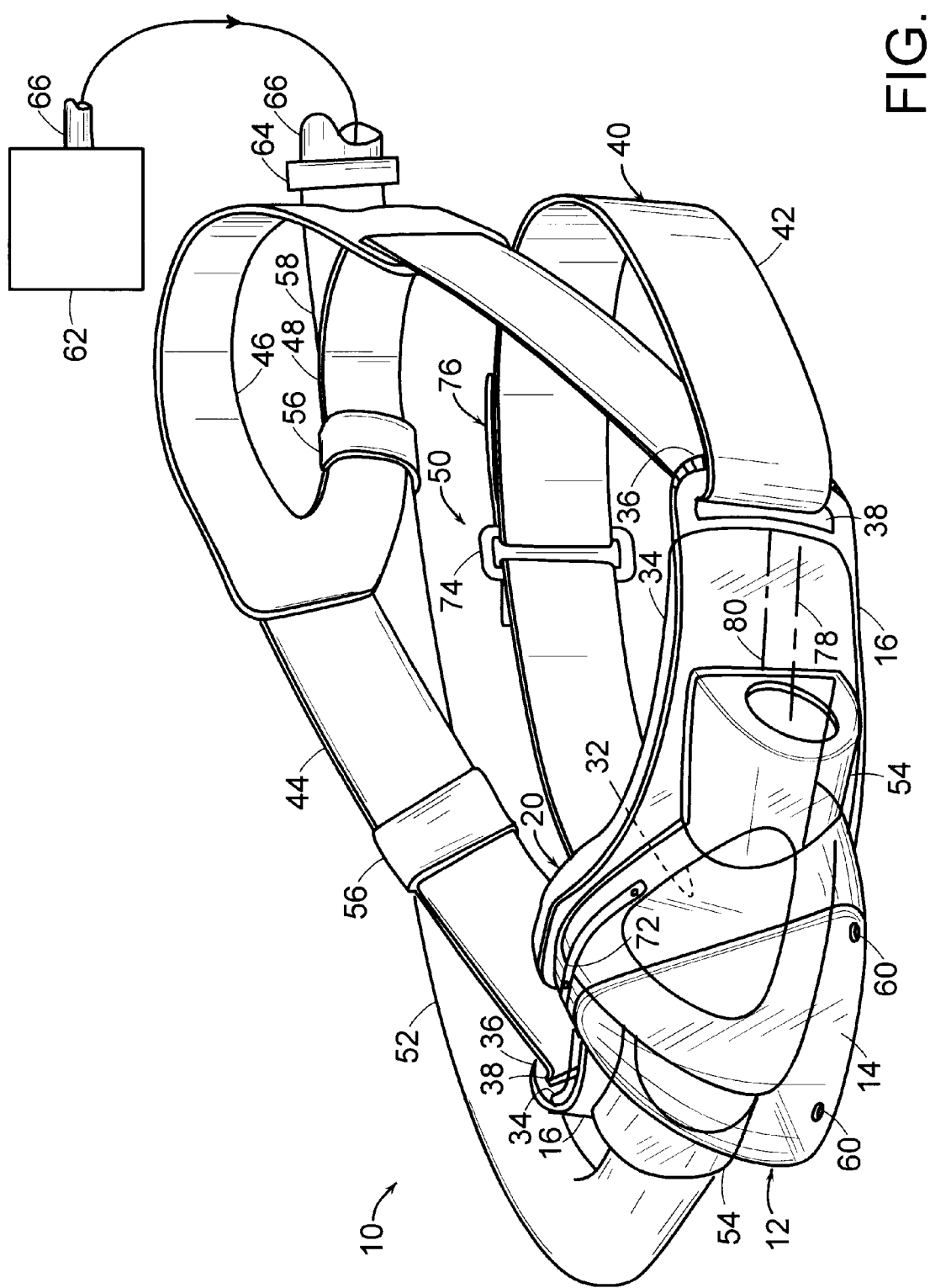
FIG. 1 is a schematic perspective view of the mask in a configuration as would be donned by a patient in accordance with an exemplary embodiment of the invention.
Figure 3:
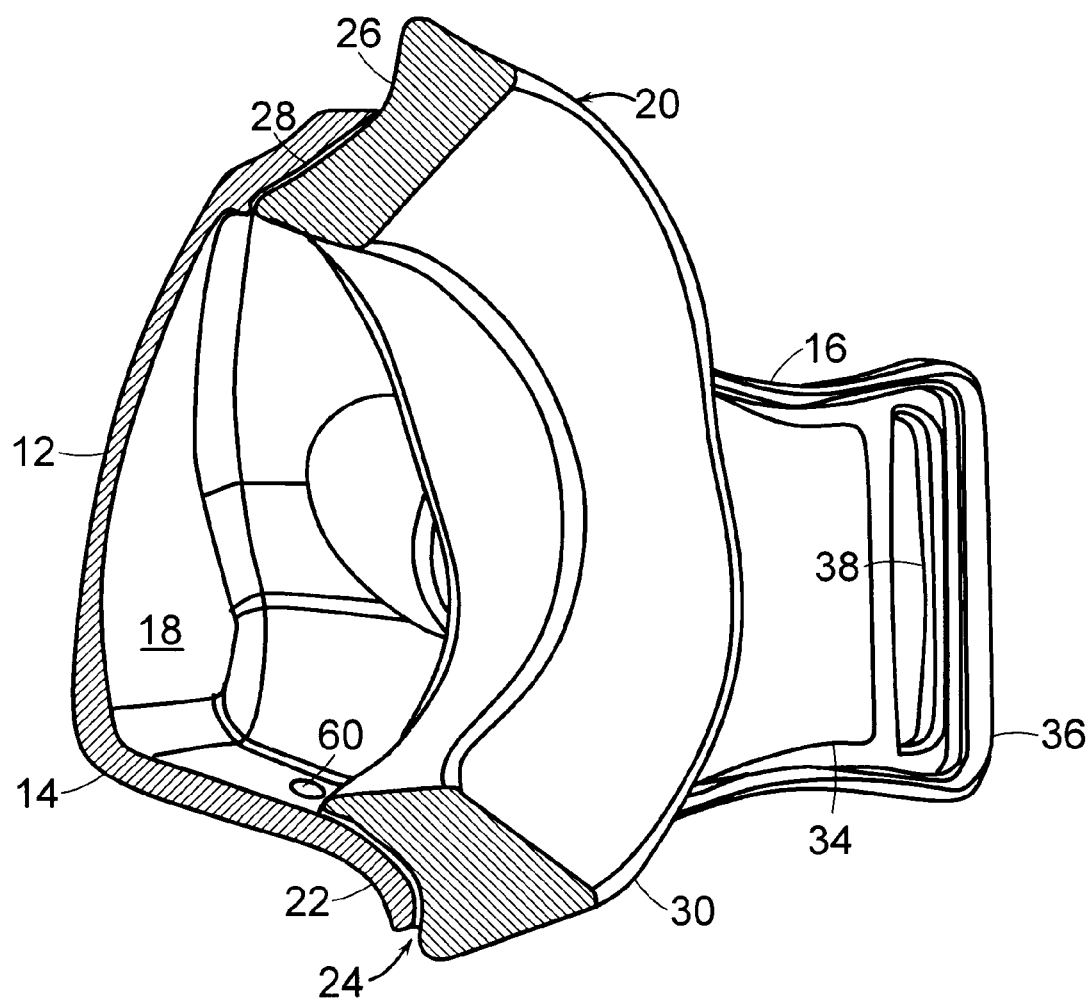
FIG. 3 is an enlarged schematic sectional perspective view of the shell and seal taken along line 3—3 of FIG. 2A in accordance with an exemplary embodiment of the invention.

Depicted in FIG. 1 is a schematic perspective view of a nasal mask 10 in a configuration as would be donned by a patient in accordance with an exemplary embodiment of the invention. The mask 10 includes a compliant shell 12 having a convex contoured portion 14 configured to surround the patient's nose and be spaced therefrom to provide a nasal area chamber 18, as best seen in FIG. 3. The chamber 18 provides a low volume reservoir of breathing gas or air supplied thereto. The shell 12 includes two symmetrically disposed, compliant side wings 16 which extend outwardly from the contoured portion 14. The wings 16 wrap around the side of the patient's face and bear on the cheek bones so that the position of the shell 12 is generally unaffected by movement of the jaw, for instance, caused by speaking, chewing, or yawning.

In order to prevent varying or uncontrolled leakage from the chamber 18 and provide a comfortable conforming fit, a soft seal 20 is provided between the shell 12 and the patient's face. The seal 20 may be manufactured of a low durometer compressible foam or other elastically compliant material; however, it has been determined that reliable sealing and increased comfort may be realized by manufacturing the seal 20 as a hollow bladder filled with a silicone medium. If desired, other mediums may be employed to fill the bladder such as gases or liquids, or emulsions of desired viscosity; however, the silicone may be molded advantageously in a predetermined configuration to provide desired sealing surfaces and contours.

As best seen in the sectional view of FIG. 3, the seal 20 has a contoured outer perimeter or surface 26 which mates with an inner surface 28 of the contoured portion 14 along a perimeter 22 thereof. In an exemplary embodiment, mating surfaces 26, 28 are attached by bonding. Other attachment methods may be employed, either alone or in combination with bonding. For example, mechanically interlocking features, such as a tapered dovetail or flange, could be employed with mating recesses. Whichever attachment method is provided, it is desirable that there be substantially no leakage of gas from the chamber 18 through the interface 24 between the seal 20 and the shell 12. A contoured inner perimeter or surface 30 of the seal 20 is tapered to provide minimal resistance to deformation when biased into contact with the nasal area of the patient thereby providing an effective seal therewith with minimal biasing force.

Figure 2A:
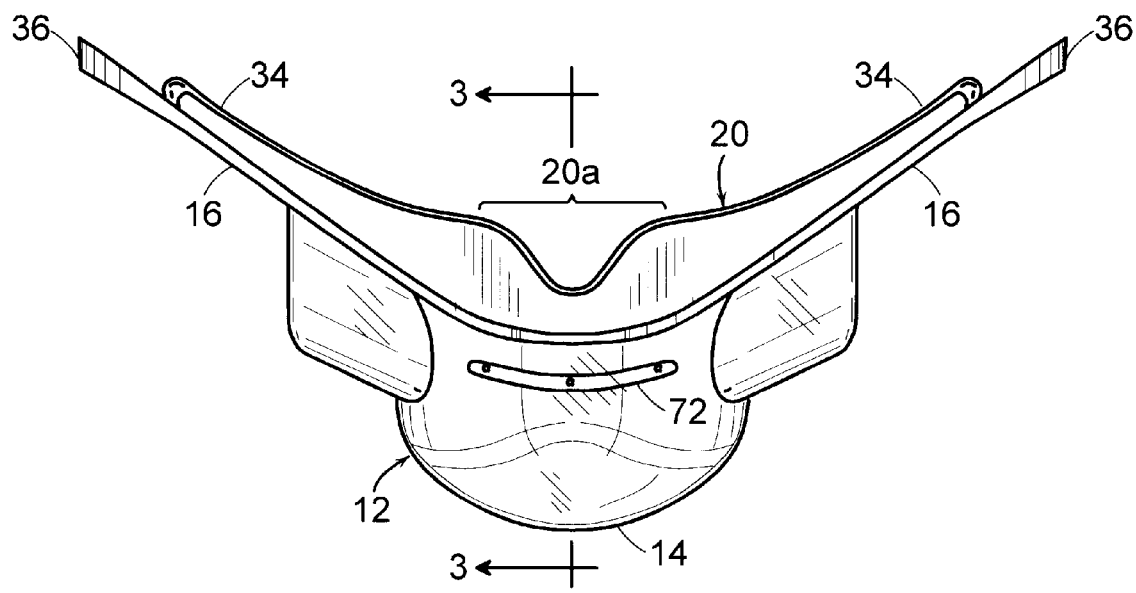
FIG. 2A is a schematic top plan view of the shell and seal in accordance with an exemplary embodiment of the invention.
Figure 2B:
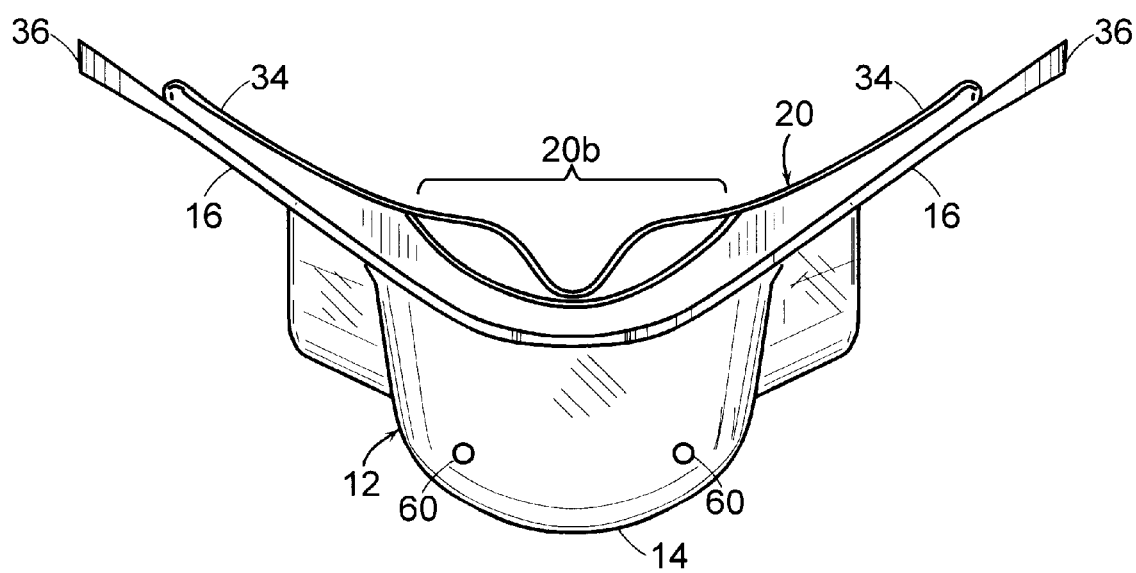
FIG. 2B is a schematic bottom plan view of the shell and seal in accordance with an exemplary embodiment of the invention.

Referring now to FIGS. 2A and 2B in conjunction with FIG. 1, the configuration of the seal 20 may be appreciated. The seal 20 is generally triangular in shape and forms a triangular shaped aperture 32 sized to circumscribe the patient's nose. The seal 20 includes outwardly extending vertices 34 adapted to match substantially the configuration of the wings 16 of shell 12. Accordingly, the seal 20 acts both to seal the chamber 18 and provide a relatively large contact area between the mask 10 and the patient's face. The large contact area provides enhanced sealing, since leakage paths along the wings are lengthy, and also provides a more reliable, comfortable fit since retention force is distributed over a large area, as will be discussed in greater detail hereinbelow.

In order to provide additional assurance of sealing around the complexly contoured area proximate the bridge of the nose, a plastically deformable nose clip 72 may be embedded in or attached to the contoured portion 14 of the shell 12 thereat. Close conformance of the shell 12 to the patient's nose bridge also provides additional support which helps to prevent slippage or shifting of the shell 12 on the patient's face. Additionally, as best seen in FIGS. 2A and 2B, respectively, the seal 20 is molded to provide a nose bridge contour 20a and an upper lip contour 20b to match the patient's nasal area and provide additional assurance of sealing and comfort.

Respective distal ends 36 of wings 16 each include a slot 38 which captures retention strap 40. The slots 38 are sized to permit sliding passage of the strap 40 therethrough. The strap 40 can be manufactured from a variety of materials and in various configurations to provide the desired biasing of the shell 12. In an exemplary embodiment depicted in FIG. 1, the strap 40 is configured as an endless loop when assembled to the shell 12. The strap 40 is typically manufactured as a linear band with an adjustable connection feature 50 such as a clasp or hook and loop fastener as will be discussed in greater detail hereinbelow. After passing the free ends of the band through the slots 38, the connection is made to form the loop. Depending on the mode of manufacture, the strap 40 may include several separate elements of the same or dissimilar material which are stitched together or otherwise attached to one another to form an assembly.

Once assembled to the shell 12, the strap 40 exhibits a lower portion 42 directed to wrap around the back of the neck, cradling the nape. The remainder of the strap 40, upper portion 44, is oriented to cradle the patient's head. To enhance support of the shell 12 and advantageously distribute the retention force over a relatively large area, the upper portion 44 can be bifurcated along a limited extent thereof into a top band 46 and a rear band 48. The top band 46 passes over the top of the patient's head and the rear band 48 around the rear of the head.

The adjustable connection 50 may be disposed advantageously along the lower portion 42 to facilitate access and adjustment of overall strap length by the patient. In an exemplary embodiment, the adjustable connection 50 is a captured rectangular "D" ring 74 through which a free end of a hook and loop fastener combination 76 slidingly passes. As may be readily appreciated, a second adjustable connection may be provided at another location. For example, two adjustable connections 50 may be provided along the lower portion 42 proximate side wings 16 to facilitate adjustment by either hand; however, since the strap 40 slides freely through the wing slots 38 and the free end of the hook and loop fastener combination 76 slides freely through ring 74, adjustment of the strap length at any single location is all that is required. Both lower and upper strap portions 42, 44 are adjusted simultaneously. The patient need only pull on the free end of the fastener combination 76 to adjust strap tension then press the hooks and loops together to retain the desired tension. Hook and loop fasteners provide good retention and are easy to adjust, even when out of view of the patient. The strap 40 may be made of an elastically compliant material, in full or in part, and may further include soft padding disposed proximate the patient to increase comfort and lessen the likelihood of irritation or chafing.

A length of flexible conduit 52 is provided which extends from an inlet 54 on the contoured portion 14 of the shell 12 to a location remote therefrom, for example, the top or rear of the patient's head. As depicted, the conduit 52 is supported at several locations along the strap 40 by a plurality of spaced retainers 56. In simplest form, the retainers 56 may be loops of rigid or preferably compliant material affixed to or captured by the strap 40. The retainers 56 are sized to permit sliding axial movement of the conduit 52 relative thereto, while maintaining the conduit 52 in close proximity to the strap 40. As depicted in FIG. 1, the conduit 52 is supported by the retainers 56 from a distal end 58 thereof to a location proximate the side wing 16; however, merely one retainer 56 at the distal end 58 has been found to function in an advantageous manner. The distal end 58 may be connected to a source 62 of pressurized air or therapeutic gas by means of a connector 64 or other coupling and source conduit 66.

The source 62 is depicted schematically and could be any of a variety of configurations including, but not limited to, a constant flow air pump, a responsive variable flow air pump, a pressure regulated oxygen tank, etc. In order to attenuate the transmission of forces and torques from source conduit 66 to mask conduit 52, connector 64 may be of the swivel or ball-in-socket variety. Additionally or alternatively, the mask conduit 52 may be made more compliant than the source conduit 66, for example, by having a thinner wall or reduced lumen diameter relative to the source conduit 66. A more compliant material or more flexible wall corrugation configuration could also be provided. Further, since the mask conduit 52 is pressurized, supported, and constrained, it need not be as structurally robust as a conventional supply conduit which must withstand relatively long, unsupported spans and which is routinely subject to twisting, stretching, and crushing in use.

The contoured portion 14 of the shell 12 is provided with two symmetrically disposed inlets 54 in fluid communication with the nasal chamber 18. Any of a variety of connections can be provided between the inlet 54 and conduit 52; however, it is desirable that the connection is leakproof for the pressures and flows anticipated. Other desirable features include low cost, low weight, and rapid connection and disconnection of the conduit 52 without the need for tools. In simplest form, the inlet 54 may be a short length of tubing of an appropriate diameter to mate with the conduit 52. If desired, the conduit 52 could be bonded directly to an inlet 54 to form an inseparable assembly therewith precluding the cost and weight associated with additional connective structure.

As depicted in FIG. 4, two inlets 54 are provided, solely one of which is connected to a supply conduit 52. In alternative embodiments, a second conduit (not depicted) could be provided attached to the same or different gas source. For example, one conduit 52 could be used to supply pressurized air to a first inlet 54 while another conduit 52 supplies a therapeutic gas such as oxygen to the other inlet 54. Alternatively, an inlet 54 could be connected with a conduit 52 to diagnostic equipment for measuring pressure in the chamber 18 or other parameter of interest. When not in use, extra inlets 54 could either seal automatically, for example by provision of a flap within the chamber 18 or inlet 54, or manually, for example by insertion of a plug therein.

The location and orientation of the inlets 54 are selected to provide a low profile connection with one or more supply conduits 52. By maintaining an inlet connection close to the wing 16 and orienting a centerline 78 of the inlet 54 substantially parallel to a centerline 80 of the wing 16, the supply conduit 52 is maintained in close proximity to the wing 16. Further, and as will be discussed in greater detail hereinbelow, torques induced in the shell 12 due to forces transmitted by the conduit 52 can be kept to a minimum. By minimizing induced torques and forces, retention forces applied to the shell 12 by the strap 40 can be minimized thereby improving patient comfort. The inlets 54 may optionally include flow diverters (not depicted) therein to direct the flow entering the chamber 18 toward or away from the nostrils, as desired.

The shell 12 may also include one or more outlets 60 disposed in the contoured portion 14, as best seen in FIG. 2B. The outlets 60 provide a constant controlled venting of the chamber 18 and provide for exhaust of exhalation. The outlets 60 are provided on the bottom of the shell 12 to facilitate draining of any moisture in the chamber 18. When the mask 10 is used in combination with a variably regulated air supply responsive to patient breathing, such as those used in sleep apnea treatment systems, the outlets 60 may be mere apertures, as depicted, to ensure a constant bleed flow. In other applications, outlets 60 may include check valves to prevent flow into the chamber 18 during inhalation or relief valves which vent the chamber 18 when pressure therein exceeds a predetermined value.

The various elements of the mask 10 cooperate to ensure maintenance of the sealed chamber 18 around the nasal area of the patient by minimizing external forces on the shell 12. By providing a compliant conduit 52 and supporting the conduit 52 on the strap 40 with one or more retainers 56, forces associated with the weight and stiffness of the source conduit 66 are significantly attenuated. When the patient moves her head, these external forces are reacted by the flexible mask conduit 52 and the resiliency of the retention strap 40. A significant amount of force resulting from movement of the patient's head which would otherwise be induced in the shell 12 is effectively attenuated. To the extent that the mask conduit 52 transmits the minimal remaining force to the shell inlet 54, the inlet 54 is situated and oriented advantageously to further minimize the potential for displacement of the shell 12 and resulting leakage. As will be discussed next with respect to FIGS. 4A–4C, forces and torques induced in the shell 12 at the inlet 54 are minimized or eliminated by orientation and disposition of the inlet 54 in an advantageous manner.

Figure 4A:
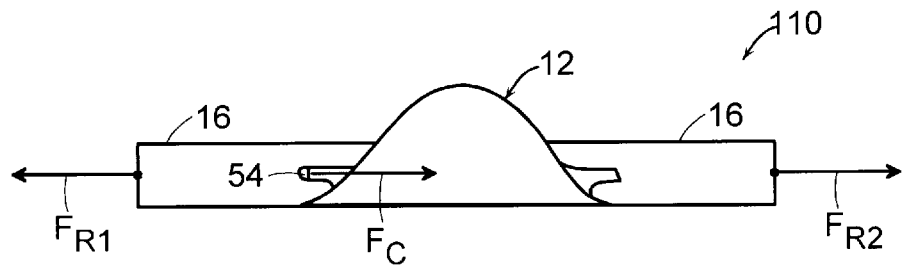
FIG. 4A is a free body diagram model of the mask shell depicting exemplary induced and offsetting loads from a frontal view in accordance with an exemplary embodiment of the invention.

Referring now to FIG. 4A, depicted is a free body diagram model 110 of the shell 12 from a frontal view corresponding to a conduit load or force, $F_c$, applied along the axis of the conduit 52 in the direction of the patient's nose. This direction corresponds to the direction of force applied when the conduit 52 is inserted into inlet 54. The reaction forces applied by the strap 40 to the shell 12 at the wing distal end slots 38 are shown as $F_{R1}$, and $FR_{R2}$. These reaction forces are the net reaction forces, it being realized that each net reaction force is the vector sum of reaction force components lying in the general direction of each of the lower neck strap 42 and upper head strap 44.

While the shell 12 is compliant, it is substantially inelastic insofar as it will not stretch appreciably under the loads encountered during normal usage. The shell 12 can therefore be modeled locally as a planar rigid body which reacts forces without deformation. As may be readily appreciated from FIG. 1, the inlets 54 are aligned with the centerlines 80 of respective side wings 16. Accordingly, since the conduit force $F_c$ is applied along the line of action of the retention forces $F_{R1}$ and $F_{R2}$, the moment arm length is zero and no torque is induced in the mask. The shell 12, therefore, will not lift off of the patient's face and the chamber seal will remain intact. For an extraordinarily large conduit force $F_c$ which starts to displace the shell 12 circumferentially around the patient's head, shear forces caused by deformation in the seal 20 would arrest the displacement due to the large contact area of the seal 20 with the patient's face. Further, circumferential displacement of the shell 12 is markedly limited due to the snug fit of the shell 12 and seal 20 to the bridge of the patient's nose along nose bridge contour 20a. If the conduit force $F_c$ were applied in the opposite direction or if the force were applied to the other inlet 54, the analysis remains the same. Simply the direction of respective force vectors is reversed.

Figure 4B:
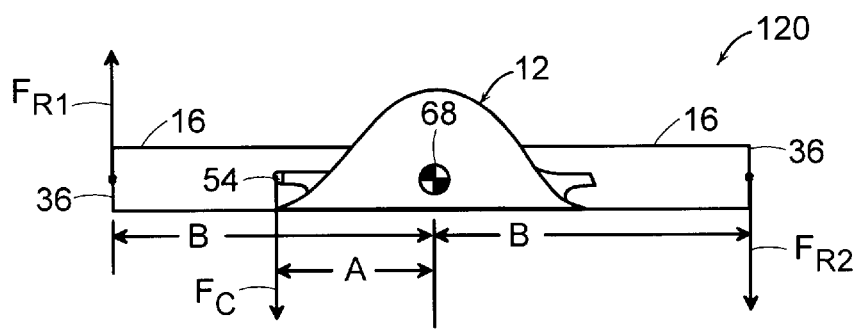
FIG. 4B is a free body diagram of the mask shell depicting other exemplary induced and offsetting loads and moment arms from a frontal view in accordance with an exemplary embodiment of the invention.

Referring now to FIG. 4B, the mask shell 12 is modeled with a conduit force $F_c$ applied in a direction normal to that depicted in FIG. 4A. This applied force is consistent with that of the weight of an unsupported mask conduit 52. Here again, since the conduit 52 is supported on the strap 40 by one or more retainers 56, any transmitted load in this direction will be minimal; however, the inlet 54 is located and oriented to minimize load induced torques and displacements caused by loading along this direction as well.

Free body diagram model 120 shown in FIG. 4B depicts the orientation and location of applied conduit force $F_c$ and retention strap reaction forces $F_{R1}$ and $F_{R2}$. Since the forces are not collinear, a moment or torque is induced in the shell 12 by the conduit force $F_c$ about pivot 68 which must be countered by the reaction forces $F_{R1}$ and $F_{R2}$. Pivot 68, aligned with a vertical centerline of the shell 12, corresponds to a vertical centerline of the nose or upper lip of the patient about which the shell 12 would attempt to rotate under the influence of the conduit force $F_c$ if not countered by the offsetting moments of the reaction forces $F_{R1}$ and $F_{R2}$. The reaction point of $F_c$ is located at the inlet 54, a distance "A" from the pivot 68; therefore, the induced torque may be calculated by multiplying $F_c$ by A. Clearly, the smaller the distance A, the lower the induced torque for a given force $F_c$ which must be offset by reaction forces $F_{R1}$ and $F_{R2}$ to prevent rotation of the shell 12. Reaction forces $F_{R1}$ and $F_{R2}$ are located equidistantly a length "B" from pivot 68 at the wing ends 36. Reaction torques may be calculated at each end 36 by multiplying each of reaction forces $F_{R1}$ and $F_{R2}$ by B. The larger the distance B, the less force need be applied to counter the torque induced by the conduit 52 at inlet 54. Accordingly, it is desirable to make distance B relatively large and distance A relatively small so that reaction forces $F_{R1}$ and $F_{R2}$ are minimized. Low reaction forces translate into low strap tension which increases patient comfort; therefore, the shell 12 is provided with long wings 16 to maximize distance B and the inlet 54 is disposed proximate contoured portion 14 to minimize distance A.

Figure 4C:
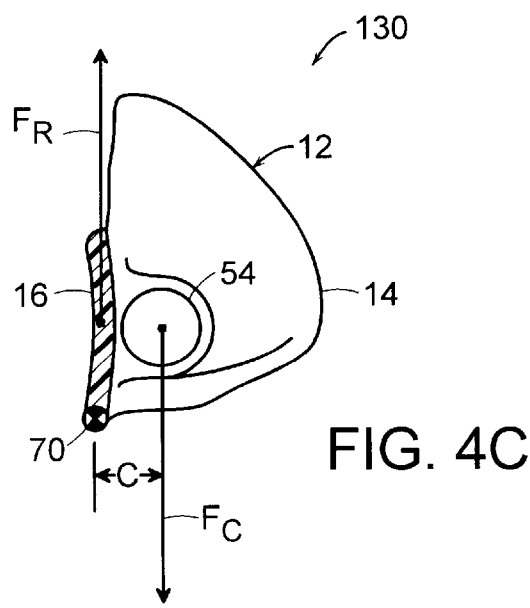
FIG. 4C is a free body diagram of the mask shell depicting exemplary induced and offsetting loads and moment arms from a side view in accordance with an exemplary embodiment of the invention.

One could eliminate the conduit induced torque in the depicted plane if the line of action of conduit force $F_c$ passed through the pivot 68, in other words if distance A were zero. This change, however, would create another conduit induced torque in a plane normal to that depicted. Since the shell 12 is not flat but includes contoured portion 14, the connection of the conduit 52 would be remote from the wing 16 and the patient's face resulting in a cantilever load. FIG. 4C is a free body diagram model 130 of the shell 12, taken from a side view, to illustrate this effect.

As shown in FIG. 4C, the mask shell 12 is modeled with a conduit force $F_c$ applied in the same direction as that depicted in FIG. 4B. Inlet 54 is disposed directly proximate side wing 16, shown in section, to minimize the moment arm distance "C" from pivot point 70. Here, pivot 70 corresponds to the upper lip of the patient about which the shell 12 would attempt to rotate, although the same analysis would apply if the pivot 70 were displaced upwardly to correspond to the bridge of the nose of the patient. Since the magnitude of the conduit induced torque is the product of $F_c$ and C, the smaller the value of C, the lesser the value of the induced torque which must be offset. As may be understood readily, since the magnitude of the induced torque is proportional to the distance of moment arm C, if the inlet 54 were disposed at the rightmost tip of contoured portion 14, both the value of C and the induced torque would be proportionally greater. Accordingly, if one were to dispose the inlet 54 at the tip of the contoured portion 14 to eliminate the conduit induced torque discussed with respect to FIG. 4B, one would induce a new torque which is more difficult to react effectively.

Referring again to FIG. 4C, since the line of action of reaction force $F_R$ reacts substantially through the pivot 70, the related moment arm is zero and an offsetting torque cannot be applied. Accordingly, strap tension must be sufficient to keep the contoured portion 14 proximate the nasal area where the nose and upper lip of the patient can support the shell 12 and provide any requisite upwardly directed force at a location displaced from the wing 16 to offset the conduit induced torque. To minimize this effect, the distance C should be kept as small as practical. Some amount of strap tension is also required to counteract the weight of the shell 12; therefore, the lighter the shell 12, the less tension required and the more comfortable a fit for the patient.

As can be recognized by those skilled in the art, forces induced in the shell 12 at the inlet 54 in vector directions other than those depicted may be modeled as a combination of the exemplary forces discussed above. Once the patient dons the mask 10 and adjusts the strap 40 and nose clip 72 to provide a comfortable, leakproof fit along the nasal area, the wrapped contour of the shell 12 and wings 16 supported by lower and upper strap portions 42, 44 effectively maintains the integrity of the sealed chamber 18. The combination of disclosed elements and features effectively counteracts any static and dynamic loading of the shell 12 due to movement of the patient's head while maintaining a comfortable fit with low strap tension.

In an exemplary embodiment of the mask 10 sized for use by an adult patient, the shell 12 may be manufactured by molding using a compliant polymer such as Pellethane™ available from Dow Corning Corporation, Midland, Mich., although other compliant polymer or vinyl materials and other processes may be employed. Distance "A" between a vertical centerline of the shell 12 and inlet 54 is between about 1.5 inches (3.8 cm) and about 2.5 inches (6.4 cm). Distance "B" between a vertical centerline of the shell 12 and wing end 36 is between about 2.5 inches (6.4 cm) and about 5.0 inches (12.7 cm). Distance "C" is minimized, being a function of conduit and inlet diameter and attachment structure, if any. Accordingly, for a 0.625 inch (1.588 cm) outer diameter conduit 52 mated with a 0.5 inch (1.3 cm) outer diameter connector made from polycarbonate and disposed in the inlet 54, distance C is a minimum of about 0.3 inches (0.8 cm). The diameter of each of the two outlets 60 is nominally 0.125 inches (0.318 cm).

The bladder of the seal 20 may be formed from polyurethane such as Platilon™, available from Elf Atochem S.A. Paris, France, and the medium disposed therein may be molded silicone commercially available from Brageol, Inc., Walnut City, Calif. The seal 20 may be bonded to the shell 12 using commercially available tetrahydrofuran ("THF") or ultraviolet cured adhesives. The seal 20 is bonded to the perimeter 22 of the chamber 18 as well as the wings 16 substantially along their entire respective lengths. Seal thickness ranges from a minimum of about 0.125 inches (0.318 cm) proximate the wings 16 to a maximum of about 1.0 inch (2.5 cm) along the perimeter 22 of the chamber 18 proximate the nose bridge contour 20a.

The conduit 52 may be manufactured from polyolefin plastomer, in a corrugated configuration, available from Smoothbore Plastics, Laguna Hills, Calif. The strap 40 may be manufactured from elastic materials such as nylon covered neoprene and Velstretch™, available from Velcro USA Inc., Manchester, N.H., and may further include optional padding, if desired. Nose clip 72 may be manufactured from thin aluminum and heat staked to the surface or preferably a recess in the surface of the shell 12. Heat staking is achieved by thermal deformation of a plurality of raised protuberances on the shell which pass through apertures in the clip 72 thereby capturing the clip 72.

While there have been described herein what are to be considered exemplary and preferred embodiments of the present invention, other modifications of the invention will become apparent to those skilled in the art from the teachings herein. For example, the mask conduit 52 could be eliminated and the source conduit 66 routed through the retainers 56 and attached directly to the inlet 54. Additionally, the configuration of the strap 40 could be replaced by other configuration strap(s) or other retention schemes such as a net which envelopes the entire head and/or neck region. Further, the shell 12 could be larger or differently shaped to create a chamber 18 for covering the mouth of a patient or both the nose and mouth. Also, the seal 20 could be manufactured as a plurality of discrete, proximately disposed elements. One element may provide sealing about the perimeter of a chamber to be sealed and one or more other elements may provide contact along remote facial areas. The molded silicone could also be directly bonded to the shell 12, without being encased in the bladder.

The particular methods of manufacture of discrete components and interconnections therebetween disclosed herein are exemplary in nature and not to be considered limiting. It is therefore desired to be secured in the appended claims all such modifications as fall within the spirit and scope of the invention. Accordingly, what is desired to be secured by Letters Patent is the invention as defined and differentiated in the following claims.

What is claimed is:

1. A nasal mask comprising:
   a shell comprising:
      a contoured portion having an interior surface and a perimeter configured to form a chamber around a nose of a patient donning said mask; and
      a pair of side wings extending outwardly from said contoured portion to extend along cheeks of a patient; and
   a seal on said shell for sealing the mask to a patient, said seal comprising:
      a contoured surface disposed about said perimeter for sealing said chamber around the nose of a patient; and
   continuous seal extending along said side wings and substantially matching a configuration of said wings so as to contact the cheeks of a patient remotely from said perimeter to increase contact area between said seal and a patient thereby reducing slippage of said mask for a given induced force.

2. The invention according to claim 1, wherein said seal has a minimum thickness of about one eighth inch.

3. The invention according to claim 1, wherein said seal has a maximum thickness of about one inch.

4. The invention according to claim 1 wherein said seal comprises a bladder.

5. The invention according to claim 4 wherein said bladder is filled with molded silicone in a predetermined configuration.

6. The invention according to claim 4 wherein said bladder is filled with a viscous medium.

7. The invention according to claim 1 wherein said seal is bonded to said shell.

8. The invention according to claim 1 further comprising:
an inlet disposed in said contoured portion for providing fluid communication with said chamber.

9. The invention according to claim 8 wherein said inlet includes a centerline which is oriented substantially parallel to one of said wings.

10. The invention according to claim 8 further comprising:
a second inlet,
wherein said first inlet, said second inlet and said wings are disposed symmetrically about said contoured portion.

11. The invention according to claim 8 wherein said inlet is connectable to a breathable gas source.

12. The invention according to claim 8 wherein said inlet is connectable to diagnostic apparatus.

13. The invention according to claim 8 wherein said inlet is sealable.

14. The invention according to claim 1 further comprising:
an outlet disposed in said contoured portion for providing fluid communication with said chamber.

15. The invention according to claim 14 wherein said outlet comprises an aperture.

16. The invention according to claim 1 wherein said shell further comprises a nose clip disposed along said contoured portion.

17. The invention according to claim 1 further comprising a strap captured by respective distal ends of said wings remote from said contoured portion for retaining said mask on a patient.

18. The invention according to claim 17 wherein said distal ends include respective slots through which said strap slidingly passes.

19. The invention according to claim 17 wherein said strap comprises a continuous loop.

20. The invention according to claim 19 wherein said loop comprises:
a first portion oriented to cradle a neck of a patient; and
a second portion oriented to cradle a head of a patient.

21. The invention according to claim 20 wherein said second loop portion is bifurcated along an extent thereof to cradle an upper and a rear portion of a patient's head.

22. The invention according to claim 17 wherein said strap has a length which is adjustable.

23. The invention according to claim 17 wherein said strap is elastically compliant.

24. The invention according to claim 17 wherein said strap includes at least one retainer for supporting a conduit connectable to an inlet disposed in said contoured portion for providing fluid communication with said chamber.

25. The invention according to claim 24 further comprising a conduit connected to said inlet, said conduit supported on said strap by said retainer.

26. The invention according to claim 25 wherein said conduit is supported loosely such that said conduit may slide axially relative to said strap.

27. The invention according to claim 25 wherein said conduit is supported on said strap by said retainer at a zone remote from said side wings.

28. The invention according to claim 27 wherein said remote zone is located proximate an upper or rear portion of a head of a patient.

29. The invention according to claim 27 wherein said conduit connects to a breathable gas source at said remote zone.

30. The invention according to claim 29 wherein said gas source comprises a second conduit and said retained conduit is more compliant than said second conduit.

31. Apparatus for treating a respiratory ailment in a recumbent or sleeping patient comprising:
a regulated supply for providing a flow of gas responsive to patient needs;
a conduit having a lumen in fluid communication with said supply; and
a mask having a connection in fluid communication with said lumen, said mask comprising:
a shell comprising:
a contoured portion having an interior surface and a perimeter configured to form a chamber around at least a nose of a patient donning said mask; and
a pair of side wings extending outwardly from said contoured portion to extend along cheeks of a patient; and
a seal on said shell for sealing the mask to a patient, said seal comprising:
a contoured surface disposed about said perimeter for substantially sealing said chamber around at least the nose of a patient; and
a continuous seal extending along said side wings and substantially matching a configuration of said wings so as to contact the cheeks of a patient remotely from said perimeter to increase contact area between said seal and a patient thereby reducing slippage of said mask for a given induced force, wherein:
said mask provides said gas flow to said substantially sealed chamber; and
said connection is disposed remotely from a nasal area and constrained such that leakage from said sealed chamber due to movement of a patient is substantially precluded.

32. The invention according to claim 31 wherein said mask includes biasing apparatus:
for preventing leakage from said sealed chamber when a patient is immobile; and
for attenuating forces induced in said mask by said conduit when a patient moves.

33. The invention according to claim 32 further comprising:
a mask conduit providing fluid communication between said connection and said sealed chamber wherein said mask conduit is routed along said biasing apparatus to permit a patient to recline without bearing thereon.

34. The invention according to claim 31 wherein said gas is air.

35. A mask for treating a respiratory ailment in a recumbent or sleeping patient comprising:
a shell for forming a chamber with a facial area of a patient; and
a seal for substantially sealing said chamber, said seal comprising:
a perimeter circumscribing an aperture formed therein, said perimeter comprising:
an outer perimeter configured to mate with said shell; and
an inner perimeter configured, at least in part, with a taper which readily deforms when biased into contact with a contour of a patient's facial area to form a seal therewith; and a continuous seal extending from said perimeter remotely from said aperture, said continuous seal for contacting cheeks of a patient remotely from said perimeter to distribute mask retention force over an area in addition to a perimeter sealing area to increase contact area between said seal and a patient thereby reducing slippage of said mask for a given induced force.

36. The invention according to claim 35 wherein said aperture is generally triangular.

37. The invention according to claim 35 wherein said aperture is sized to circumscribe a nasal or an oral area of a patient.

38. The invention according to claim 35 wherein said aperture is sized to circumscribe a nasal and an oral area of a patient.

39. The invention according to claim 35 wherein said continuous seal extends generally symmetrically from said perimeter for contact with facial areas of a patient remote from said aperture.

40. The invention according to claim 35 wherein said seal comprises molded silicone in a predetermined configuration.

41. The invention according to claim 40 wherein said seal further comprises a polyethylene bladder encasing said molded silicone.

* * * * *